(12) United States Patent
Hazelden et al.

(10) Patent No.: US 7,114,373 B2
(45) Date of Patent: Oct. 3, 2006

(54) FLUID MONITORING

(75) Inventors: Roger John Hazelden, Tamworth (GB); Kimberley Patrick Fraser Smith, Birmingham (GB)

(73) Assignee: TRW Limited, (GB)

( * ) Notice: Subject to any disclaimer, the term of this patent is extended or adjusted under 35 U.S.C. 154(b) by 0 days.

(21) Appl. No.: 11/197,780

(22) Filed: Aug. 4, 2005

(65) Prior Publication Data

US 2006/0032295 A1 Feb. 16, 2006

Related U.S. Application Data

(63) Continuation of application No. PCT/GB04/00425, filed on Feb. 4, 2004.

(30) Foreign Application Priority Data

Feb. 4, 2003 (GB) .................................. 0302519.4

(51) Int. Cl.
*G01N 11/00* (2006.01)
(52) U.S. Cl. ...................... 73/54.02; 73/1.86; 73/1.82; 73/54.41; 702/54
(58) Field of Classification Search ............... 73/54.02, 73/54.41, 1.82, 1.86; 702/54
See application file for complete search history.

(56) References Cited

U.S. PATENT DOCUMENTS 4,721,874 A * 1/1988 Emmert ...................... 310/333
4,862,384 A * 8/1989 Bujard et al. .................. 702/54
5,365,778 A * 11/1994 Sheen et al. ................ 73/54.41
5,686,661 A    11/1997 Singh et al.
5,900,690 A * 5/1999 Gipson et al. ......... 310/316.01
6,223,589 B1   5/2001 Dickert et al.
6,763,698 B1 * 7/2004 Greenwood ................ 73/30.01
2003/0233878 A1 * 12/2003 Drahm et al.

FOREIGN PATENT DOCUMENTS

WO        WO 98/01739          1/1998

* cited by examiner

*Primary Examiner*—Charles Garber
*Assistant Examiner*—Samir Shah
(74) *Attorney, Agent, or Firm*—MacMillan, Sobanski & Todd, LLC (57) ABSTRACT

An apparatus for measuring the viscosity and temperature of a fluid, for example an engine oil, comprises a transducer, which is arranged to vibrate when provided with a drive signal to produce an ultrasonic shear wave; an impedance matching layer that is inserted into the fluid and which couples at least a portion of the ultrasonic waves produced by the transducer into the fluid and from which at least a portion of the wave is reflected back to the transducer; a detector which is adapted to detect a measurement signal produced by the transducer when the reflected wave is incident upon the transducer; a control circuit which varies the frequency of the drive signal applied to the transducer and hence the frequency of the ultrasound signal; a processing means which determines the optimum frequency of the drive signal at which the measurement signal output from the transducer has its minimum amplitude; and a temperature determining means which estimates the temperature of the fluid as a function of the optimum frequency.

8 Claims, 9 Drawing Sheets

FLUID MONITORING

CROSS REFERENCE TO RELATED APPLICATIONS

This application is a continuation of International Application No. PCT/GB2004/000425 filed Feb. 4, 2004, the disclosures of which are incorporated herein by reference, and which claimed priority to Great Britain Patent Application No. 0302519.4 filed Feb. 4, 2003, the disclosures of which are incorporated herein by reference.

BACKGROUND OF THE INVENTION

This invention relates to improvements in fluid condition monitoring apparatus and methods of monitoring the condition of a fluid. It is especially, but not exclusively, suited to the measurement of the condition of engine oil such as its shear impedance (or viscosity/density) and temperature and the detection of changes in oil condition as the oil ages over time.

The condition of the oil in an engine, for example an engine of a motor vehicle, is important for the reliable operation of the engine. With recent trends in vehicle servicing causing the number of operating hours of the engine between services to increase, the oil in an engine remains in the engine for longer periods of time than ever before. Over this time the oil may deteriorate due to, for example, sooting or other particulate contamination, fuel dilution, oxidation or shear thinning. Clearly the rate at which the oil deteriorates will depend on the age of the engine and the way in which the engine is operated between services. Attempts have been made by many vehicle manufacturers to monitor the operation of the engine allowing variable service intervals to be employed.

A key property of an engine oil is its viscosity—essentially its ability to resist shear forces. This is an essential property of an oil when protecting the component parts of an engine from premature wear. When an oil acts as a lubricant between two bearing surfaces operating at high frequency the shear rates are high and so it is also logical to measure the shear viscosity of the oil at high rates of shear. This can be measured in a variety of ways. For example, U.S. Pat. No. 4,721,874 teaches the use of a transducer which oscillates at high frequency to send ultrasonic shear waves into the fluid through a wave guide. A portion of the wave will be reflected back onto the transducer at the interface between the guide and the fluid. When this reflected wave is incident upon the transducer it produces an output signal. A measurement of the amplitude of this output signal gives an indication of the shear rate (or more correctly the product of viscosity and density). Whilst this offers a useful measurement of viscosity it does not provide any information, which would enable the cause of the change to be determined. Effects such as sooting, oil dilution, oxidation and shear thinning all alter the viscosity of an oil in different ways. The applicant has appreciated that it would be advantageous to be able to distinguish between the different effects as well as measuring simple changes in viscosity. This would provide valuable information about the overall condition of an engine and not just its oil, perhaps allowing a warning to be raised of any wear or engine damage.

BRIEF SUMMARY OF THE INVENTION

According to a first aspect the invention provides an apparatus for measuring the viscosity and temperature of a fluid comprising:

a transducer, which is arranged to vibrate when provided with a drive signal to produce an ultrasonic shear wave;

an impedance matching layer that is inserted into the fluid and which couples at least a portion of the ultrasonic shear wave produced by the transducer into the fluid and from which at least a portion of the wave is reflected back to the transducer;

a detector which is adapted to detect a measurement signal produced by the transducer when the reflected wave is incident upon the transducer;

a control circuit which varies the frequency of the drive signal applied to the transducer and hence the frequency of the ultrasonic shear wave;

a processing means which determines the optimum frequency of the drive signal at which the measurement signal produced by the transducer has its minimum amplitude;

and a temperature determining means which estimates the temperature of the fluid as a function of the optimum frequency.

By impedance matching layer we mean an element which serves to minimise the amount of the ultrasound wave reflected back to the transducer. This may effectively comprise a quarter wave plate (or a plate which is an odd multiple of one quarter wave) at the frequency of the wave. The properties of the layer, i.e. thickness and refractive index, should be chosen to match the frequency used or vice versa.

The applicant has appreciated that changes in temperature alter the refractive index of the matching layer and also its thickness, both of which alter the frequency at which it acts as a quarter wave plate and hence the amount of reflected wave at the interface. Therefore the frequency of the drive signal that must be used to provide for minimum reflection will change as a function of the temperature of the impedance matching layer, and hence if the frequency is known a good estimate of the temperature of the fluid can be made.

The apparatus may include a wave guide which couples the transducer to the impedance matching layer. The wave guide may be coupled to the transducer at a first end and coupled to the impedance matching layer at its other end. The function of the wave guide is to carry the wave produced by the transducer to the fluid and also to increase the path length for the reflected signal, ensuring that the measurement signal is temporally distinct from the drive signal.

The apparatus may include a look-up table in which the estimated temperature corresponding to a determined optimum frequency is stored.

The wave guide may be provided with a reflection interface located between the transducer end and the matching layer end from which a portion of the ultrasound wave produced by the transducer is reflected back to the transducer. This will cause the transducer to produce a reference signal and a reference signal monitoring circuit may be provided for measuring the amplitude of the reference signal. This circuit may be the same circuit as the circuit which detects the amplitude of the output signal. The location of the reflection interface should be selected to ensure that the reference signal and the measurement signals are temporally distinct.

The apparatus may include a comparator which compares the amplitudes of the reference signal and its corresponding measurement signal to determine the viscosity of the fluid.

The apparatus may include a memory for storing the results of the or each measurement of viscosity that is made along with the temperature at which the or each measurement was made. Most preferably, the apparatus may include means for measuring the viscosity at different temperatures and numerous times. A table of measurements of viscosity against time at a range of different temperatures may be stored in the memory during the life of the oil.

For example, the apparatus may take measurements spaced apart by a set interval of time, such as 5 minutes apart. Alternatively, where the apparatus is adapted to measure the condition of an engine oil it may be adapted to take a first measurement when the engine is shut down and a second when it is operating. The temperature at the first measurement will often be cooler than at the second. The key feature of this approach is to map the viscosity/temperature performance of the oil when it is initially added to the engine and thereafter at frequent intervals. The frequency will depend upon the use of the engine. It is important that measurements are made at the same temperature each time or that a curve is produced that will allow extrapolation to the same temperature. The ongoing change in oil condition will be deduced from the way in which the viscosity/temperature curve changes with time.

It is also advantageous to take frequent readings when the engine oil has reached a stable hot running temperature. This will enable the effects of fuel dilution to be seen since a viscosity reading which has been lowered due to fuel dilution will increase as the fuel evaporates from the hot oil even though the oil temperature and therefore the anticipated viscosity are stable.

Continual monitoring of the sensor output will also facilitate rapid identification of sudden changes in the viscosity due to "fuel dump"; the addition of substantial amounts of fuel due to system faults. Such changes could be signalled to the vehicle diagnostics immediately.

The apparatus may include an area of memory in which is stored a first set of measurements of the viscosity of the fluid at a range of different temperatures obtained over a first period in time and a second set of measurements of the viscosity of the fluid at a range of different temperatures obtained over a second, subsequent, period in time; curve fitting means arranged to fit the first set of measurements to a first temperature/viscosity curve and the second set of measurements to a second temperature/viscosity curve; and processing means arranged to determine the cause of any viscosity changes with ageing of the fluid by comparing the curve for the second time period with the corresponding curve in the first period.

The apparatus may therefore include a processor which analyses the results stored in the memory to identify changes in the condition of the fluid caused by at least one of the following effects:

sooting (or other particulate contamination);
dilution, primarily by fuel but also by other fluids;
oxidation;
shear thinning.

The applicant has appreciated that such an analysis is possible since each effect causes the shape of a curve of viscosity/temperature to vary in a unique manner. The shape of the curve can be identified from the information in the memory.

Clearly it is an advantage to take measurements of viscosity at many different temperatures to enable the most accurate curve to be created. A curve made from measurements at 3 or 4 different temperatures has been shown to provide useful results.

The apparatus may monitor the change in shape of the viscosity/temperature curve over time and from the comparison determine the effect that has caused the change.

For example, as an oil ages its viscosity may increase due to contamination (such as sooting) or decrease due to shear thinning or dilution. Repeated measurement of viscosity at a set temperature would provide an indication of whether the viscosity has increased or decreased over time, allowing a single effect to be identified. It may not, however, show up any change if both effects are present. By taking several measurements across a range of temperatures the two effects could be identified because of the way that they alter the shape of the temperature/viscosity curves. This invention exploits this temperature dependence.

Of course, it is possible that rather than measure viscosity the invention may simply measure shear impedance of the fluid. The shear impedance is the product of shear viscosity and density, and it is therefore a trivial step to go on to derive viscosity from this. Also, rather than ultrasonic waves a lower frequency could be used for the waves such as an acoustic wave.

According to a second aspect the invention provides an apparatus for measuring the viscosity of a fluid comprising:
a transducer, which is arranged to vibrate when provided with a drive signal to produce an ultrasonic wave;
a wave guide which is coupled to the transducer at a first end and is inserted into the fluid to be measured at an opposing end and which couples the ultrasonic waves produced by the transducer into the fluid and from which at least a portion of the wave is reflected back along the wave guide to the transducer, the wave guide including a step decrease in cross section along its length;
a detector which is adapted to detect a reference signal produced by the transducer in response to a portion of the wave being reflected from the step in the guide and a measurement signal produced by the transducer in response to a portion of the wave being reflected from the end of the wave guide; and
a processor which compares the amplitude of the reflected and measurement signals and determines the viscosity of the fluid therefrom.

The wave guide may comprise a cylindrical rod which may have a step change in diameter along its length which defines the surface from which the reference signal is reflected. It may be a solid wave guide, a suitable material being quartz or aluminium.

Of course, other sources of reference reflection could be provided, such as a groove provided around the wave guide. This would also present an obstruction in the path of the wave produced by the transducer that will create a reflection.

According to a third aspect the invention provides a method of identifying the condition of a fluid comprising the steps of:
measuring the shear impedance and/or viscosity of the fluid at a range of different temperatures at a first period in time and fitting the measurements to a first temperature/viscosity curve;
measuring the shear impedance and/or viscosity of the fluid at a range of different temperatures at a second, subsequent, period in time and fitting the measurements to a second temperature/viscosity curve; and
from any changes in the shape of the curve for the second time period compared with the corresponding curve in the first period determining the cause of any viscosity changes with ageing of the fluid.

Different contaminants and/or degradation effects change the viscosity/time curves in different ways, allowing them to be uniquely identified from the measurements that are obtained. The curves therefore allow the cause of any changes in the fluid to be identified.

The curves (which for the avoidance of doubt may be expressed as a linear function in some cases) may be analysed by fitting them to a set of predefined reference curves or traces obtained from a control sample of oil which has been subjected to a known contamination or degradation.

Curves may be produced at third and fourth or more time periods throughout the useful life of the fluid, and the method may analyse the change in shape of the curves over time as part of the basis for determining the cause of ageing of the fluid.

By period of time we may mean a period of a few seconds up to a few days or weeks, depending on the rate at which the fluid is expected to age. If the fluid is in an environment where it is expected to age slowly the time periods can be relatively long compared with fluid in an environment where rapid ageing is expected.

Also, the time spacing between time periods will depend on the application of the fluid. The first and second time periods could be many days or months apart if ageing is slow, or closer together in applications where the fluid is ageing rapidly.

The method is especially suitable for the monitoring of the condition of an engine oil, perhaps in situ within an engine. The method may be carried out using the apparatus of the first and/or second aspects of the invention.

The method may include a step of obtaining the measurements using sensors attached to the engine and storing the results in a memory attached to the vehicle. The results may be downloaded from the memory to a remote computer for analysis, perhaps when the engine is stopped for a service. Alternatively, the results may be regularly analysed between services by an on-board processor fitted to the vehicle. A service may be scheduled for a time determined at least in part by the results of this on-board analysis.

Other advantages of this invention will become apparent to those skilled in the art from the following detailed description of the preferred embodiment, when read in light of the accompanying drawings.

DETAILED DESCRIPTION OF THE INVENTION

Figure 1:
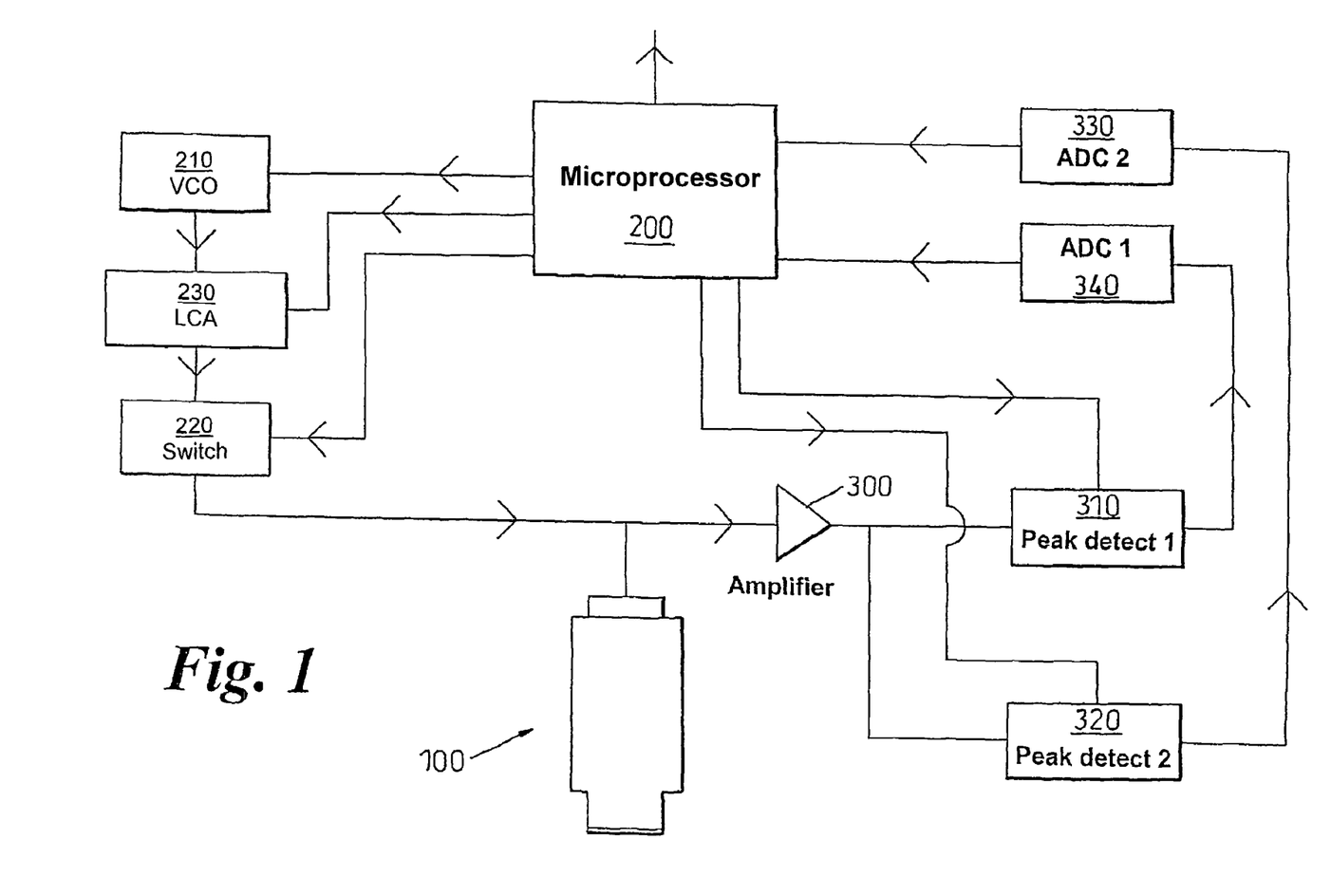
FIG. 1 is an overview of a measuring apparatus in accordance with the present invention.

Referring now to the drawing, there is shown, in FIG. 1, an apparatus that includes a transducer 100 which is inserted into a fluid to be measured and a dedicated electronic circuit which is coupled to the transducer 100.

Figure 2:
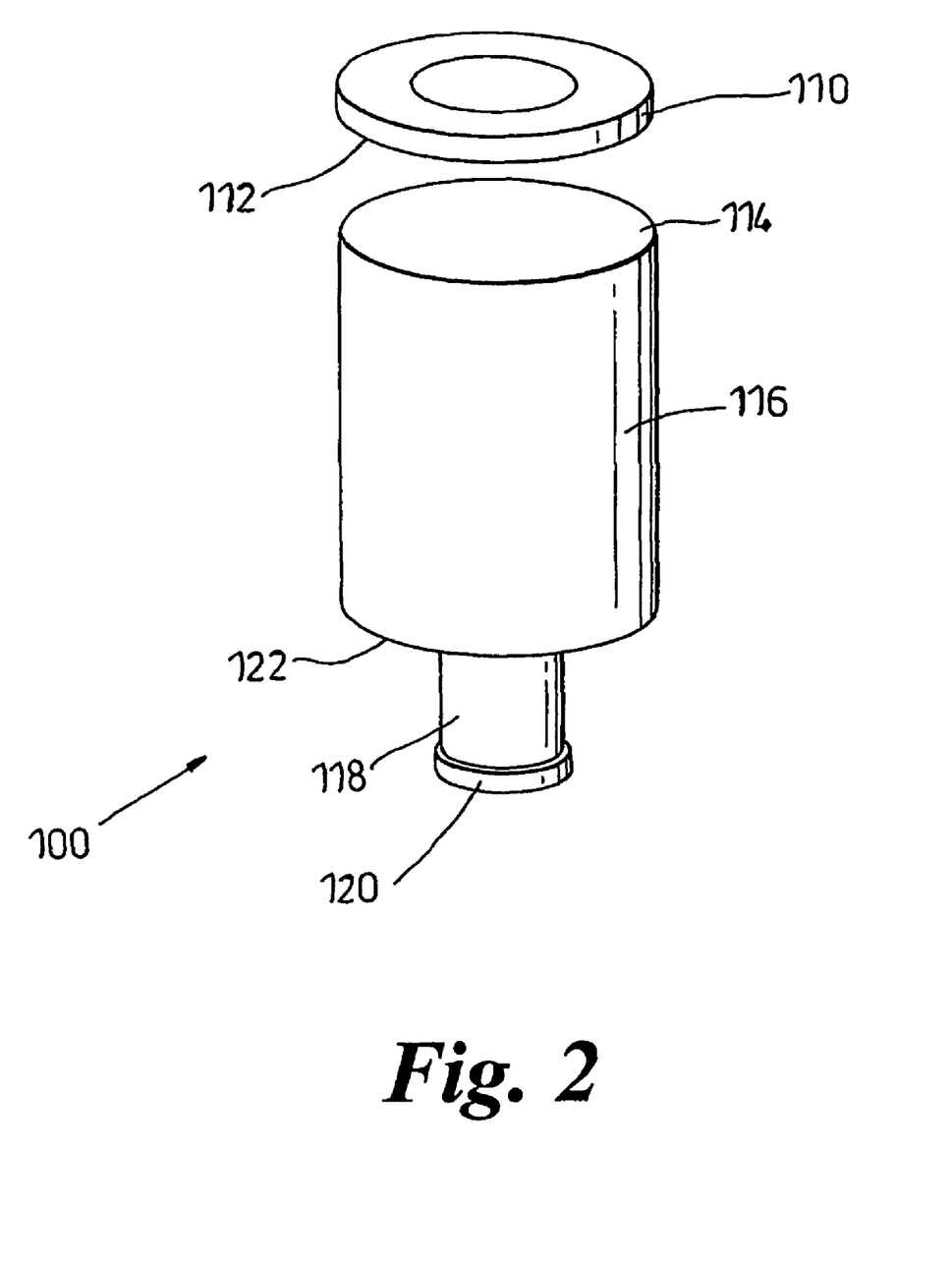
FIG. 2 is an enlarged view of a transducer which forms a part of the apparatus.

The transducer 100 is shown in an enlarged exploded view in FIG. 2 of the accompanying drawings. It comprises an annular piezo-electric element 110 that produces a shear wave when driven by an electrical signal produced by the electronic circuit. It is a shear mode device and is driven at right angles to the direction of polarisation at a frequency of approximately 5 MHz to produce an ultrasonic shear wave. A face 112 of the piezo-electric element is coupled using a suitable adhesive to one end 114 of a wave guide 116. In this example the waveguide comprises a cylindrical rod of solid material such as glass or aluminium. The waveguide 116 directs the ultrasonic shear waves from the piezo-electric element down the rod to its free end 118 which is immersed in the fluid to be measured. The free end 118 also carries an impedance matching layer 120. The layer is bonded to the end 118 of the rod which helps to couple the maximum amount of energy from the wave guide into the fluid by acting as a quarterwave plate. It comprises a thin layer of material such as a polymer with a thickness and shear impedance that produces a zero total reflection at one particular frequency of nominally 5 MHz.

The piezo-electric element 110 used as a transmitter also functions as a detector and produces an electrical signal whenever a shear wave is incident upon it. Whilst most of the wave generated by the piezo-electric element 110 is passed into the fluid through the impedance matching layer 120 some is reflected by total internal reflection and this is channeled by the wave guide 116 back to the face of the piezo-electric element 110. As this measurement reflected wave hits the piezo-electric element 110 it causes the piezo-electric element to produce a measurement signal.

The wave guide 116 is provided with a step change in diameter along its length such that the diameter of the wave guide end which carries the piezo-electric element 110 is greater than the diameter of the end which carries the impedance matching layer 120. This step change provides an annular reflecting surface 122 from which some of the wave generated by the piezo-electric element 110 is reflected back towards the piezo-electric element 110. As this reference reflected wave hits the piezo-electric element 110 it causes the piezo-electric element to produce a reference signal.

Figure 3:
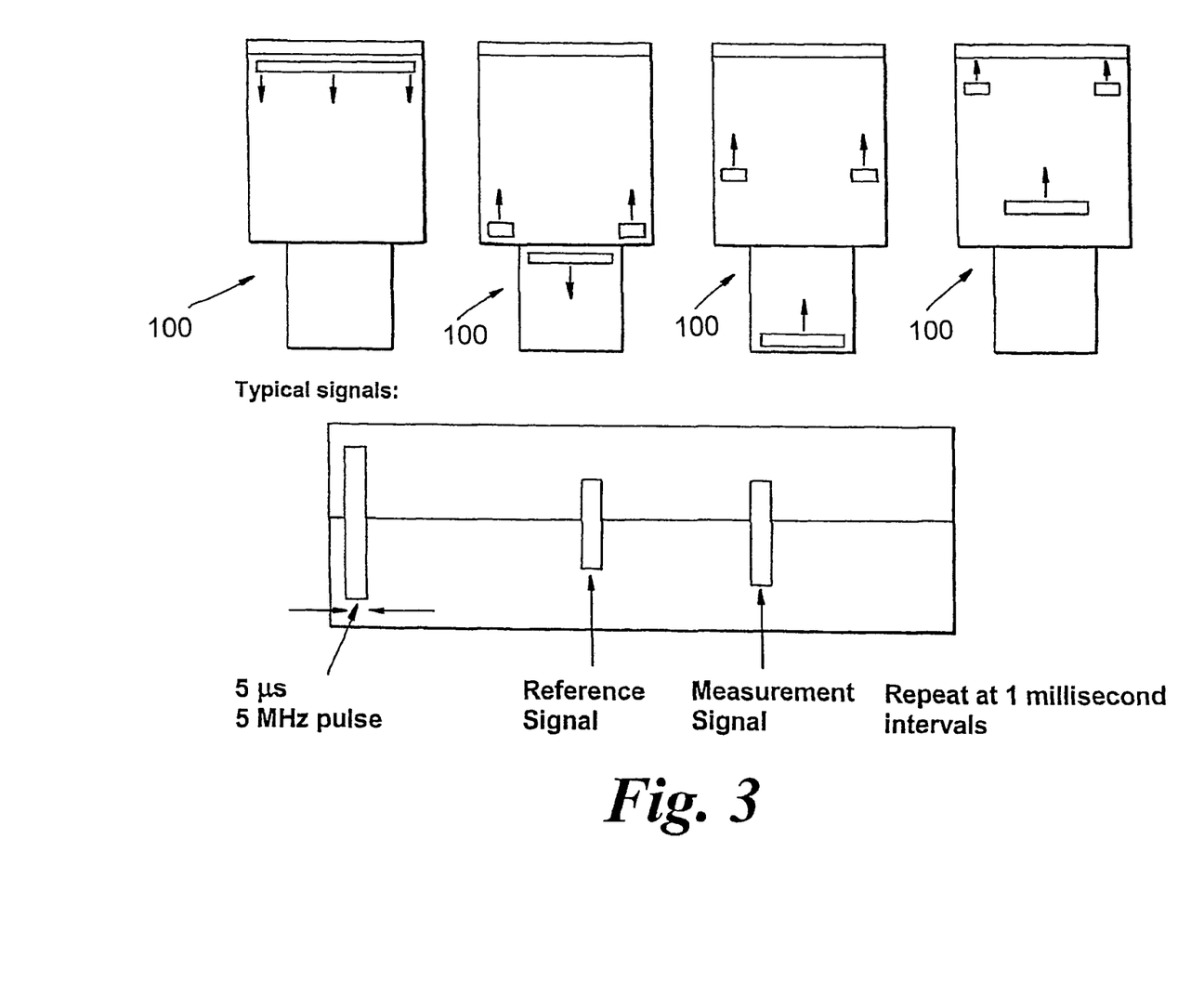
FIG. 3 illustrates the passage of a wave produced by the transducer and the reflected reference and measurement waves this causes through the transducer illustrated in FIG. 2.

The passage of the wave produced by the piezo-electric element 110 and reflected reference and measurement waves are illustrated in FIG. 3 of the accompanying drawings.

The dedicated electronic circuit performs the following functions:
  to generate the drive signal and apply it to the transducer
  to isolate the transducer from the generator when not driven
  to accept/detect the measurement and reference signals from the transducer
  to measure the amplitudes of the signals; and
  to calculate the ratios of these signals and determine the viscosity of the fluid from the result of the calculation.

As will become apparent the circuit also controls the frequency and amplitude of the drive signals allowing an estimate of fluid temperature to be made without the need for a dedicated temperature sensor to be provided.

The dedicated electronic circuit, as shown in FIG. 1, comprises a selection of analog and digital components which are controlled, in the preferred embodiment, by a microprocessor 200. Alternately the invention also contemplates that the electronic components may be controlled by a micro-controller (not shown). The use of a microprocessor 200 affords the designer a considerable degree of design freedom. It also allows the operation of the apparatus to be integrated with other systems that may be present such as an engine management system used to control an engine to which fluid under measurement is added.

In use, the transducer 100 is driven by a plused drive signal produced by a Voltage Controlled Oscillator (VCO) 210 operating at approximately 5MHz. The exact frequency is controlled by the microprocessor 200 which varies the control voltage applied to the input of the VCO 210. Each drive signal pulse comprises a burst of electrical energy of approximately 5 microseconds duration, repeated at approximately 1 millisecond intervals. The timing and duration of these pulses is controlled by the microprocessor 200 which opens and closes a gate or switch 220 through which the wave form produced by the VCO 210 must pass to reach the piezo-electric element 110. The switch 220 also serves to isolate the piezo-electric element 110 from the VCO 210 after the drive signal pulse has ended to prevent transducer loading by the VCO 210. The signal is also passed through a Level Control Amplifier (LCA) 230 which is again controlled by the microprocessor 200.

The resulting reference and measurement pulses produced by the piezo-electric element 110 will also be of approximately 5 microseconds duration and are detected by a detection circuit. The detection circuit comprises an amplifier 300 which boosts the low amplitude output from the piezo-electric element 110 to a higher level suitable for processing. Two peak detectors 310 and 320 detect the first pulse and the second measurement pulse produced and pass them through respective analogue to digital converters 340 and 330 to the microprocessor 200 where they are initially stored in a buffer memory (not shown) for subsequent processing and/or analysis.

The length of the wave guide 116 is chosen together with the duration of the drive pulse such that the piezo-electric element 110 produces a reference output signal and a subsequent measurement signal which do not overlap temporally. The spacing between the reference and measurement signals can be increased by increasing the length of the wave guide.

Figures 4, 5:
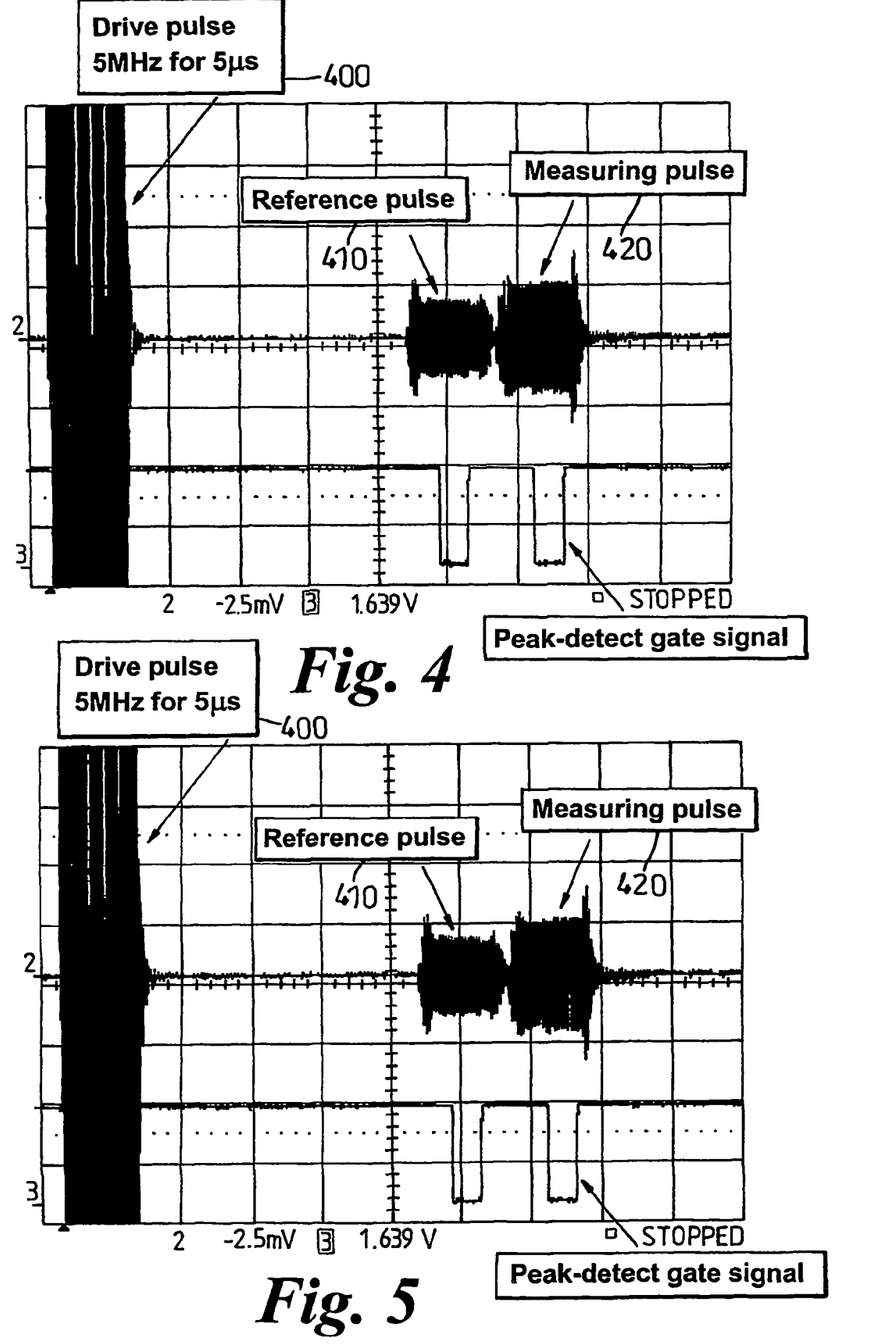
FIG. 4 of the accompanying drawings shows typical signals at the piezo device in air.
FIG. 5 of the accompanying drawings shows typical signals at the piezo device in oil.

FIG. 4 of the accompanying drawings shows typical signals at the piezo device in air. A drive pulse 400 can be seen, followed by a time delay (due to the wave guide) before the reference pulse 410 and the measurements pulse 420 arrive. The Figure also shows the timing of the peak detect gate signal generated by the microprocessor.

FIG. 5 shows the same signals but with the sensor end immersed in oil. Note that the measuring pulse amplitude has reduced while the reference pulse is unchanged.

Figure 6:
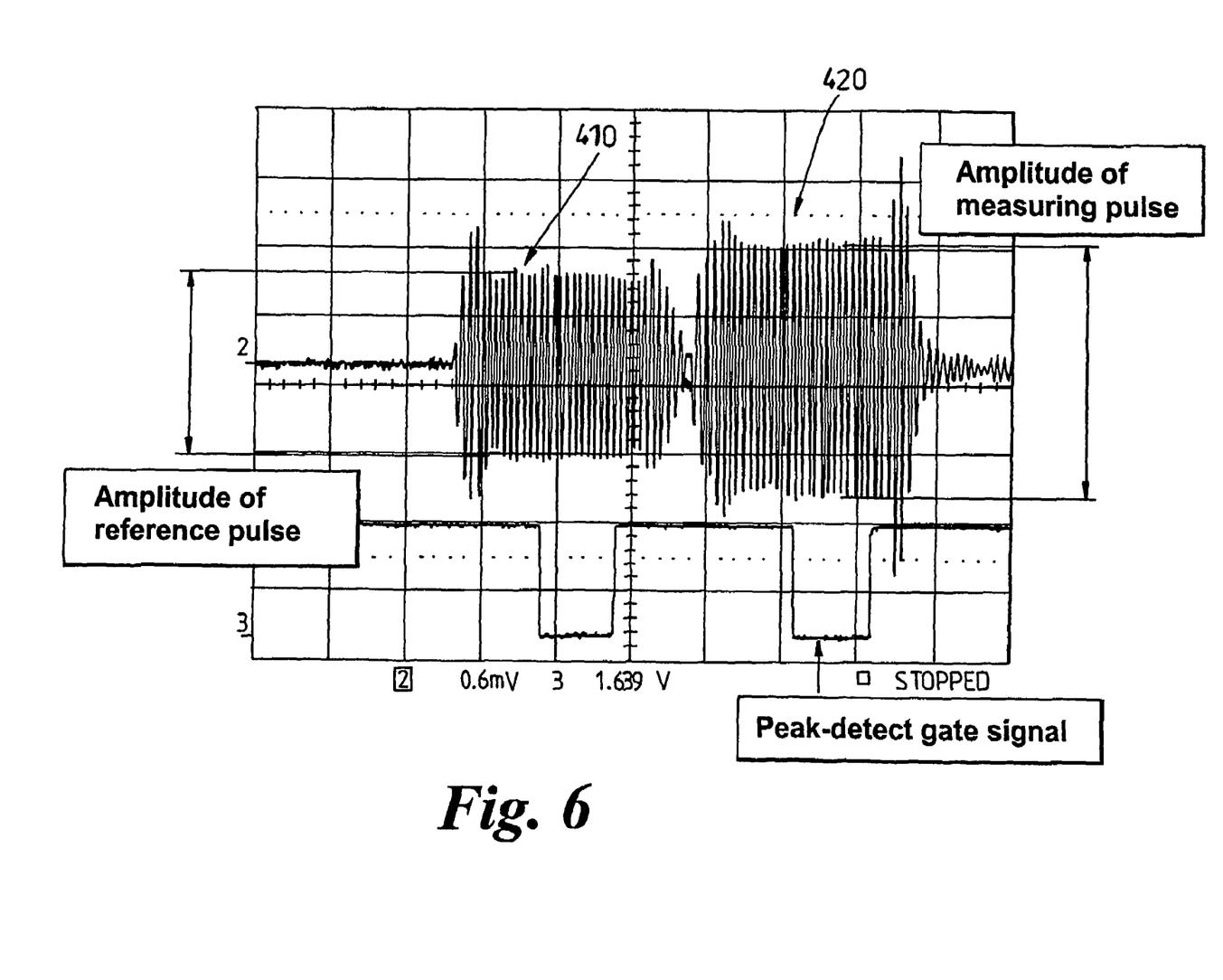
FIGS. 6 and 7 are enlarged plots of measuring pulse amplitude against time recorded in air and in oil respectively.
Figure 7:
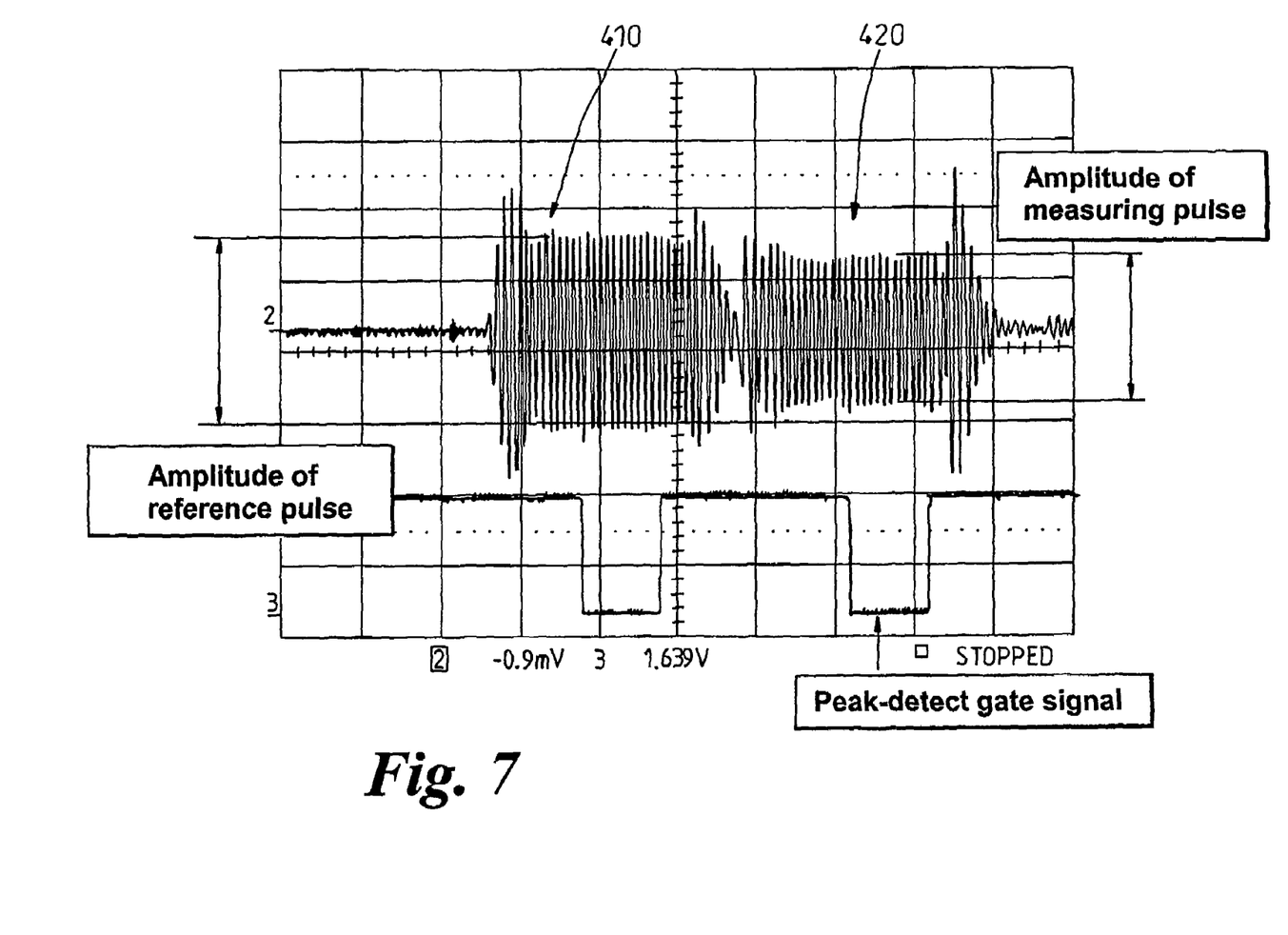

The reflected pulses 410, 420 from the reference surface and the measuring surface pass to the amplifier 300. This has a high input impedance to avoid excessive loading of the transducer output, and the output then passes to the two gated peak detectors. These detect the peak amplitude of the signal envelopes returned from the reference and measuring pulses 410,420. FIGS. 6 and 7 are expanded views of the signals with the sensor in air and oil respectively.

The amplitude of the reference signal 410 will remain substantially constant for a given amplitude of drive signal applied to the transducer 100. The amplitude of the measurement signal will vary with the viscosity of the fluid. It sill also be observed that by sweeping the frequency slightly around its nominal 5 MHz value a minimum amplitude will be observed. This effect is due to changes in the physical properties of the impedance matching layer 120 with temperature.

The microprocessor 200 varies the exact frequency of the VCO 210 in 1 kHz or 100Hz steps. A series of drive pluses are sent to the transducer 100 and the amplitude of the measurement pulse 420 corresponding to each one of the drive pulses is monitored by the microprocessor 200 to identify the frequency at which the amplitude is minimum. The microprocessor 200 then reads out a temperature value from a look-up table stored in an area of the memory attached to the microprocessor 200.

Finally, the microprocessor 200 compares the minimum amplitude with the amplitude of the reference signal 410 to determine the viscosity of the fluid. The viscosity may be determined from a simple ratio of the reference pulse 410 and measurement pulse 420 amplitudes, with the resulting ratio being used as a key to a look-up table stored in the memory.

Obtaining measurements of viscosity and temperature also allows the apparatus to perform an analysis of the ageing of the oil (or any other fluid that is under test). To do so, the microprocessor 200 must first store a set of viscosity readings obtained at different fluid temperatures before the fluid is subjected to any wear. A typical set would be measured over a first time period of perhaps a few hours or days across a range of 20–100 degrees centigrade. After an elapsed time of say a month a second set of measurements of viscosity are made across the same temperature range. These will also be measured over a set period of time of say a few hours. The two sets of data are then each fitted to a curve. If the oil has aged the curves will be different and the change in shape of the curve will be dependent upon the cause of the ageing which can be identified by the application of appropriate algorithms by the microprocessor.

Figure 8:
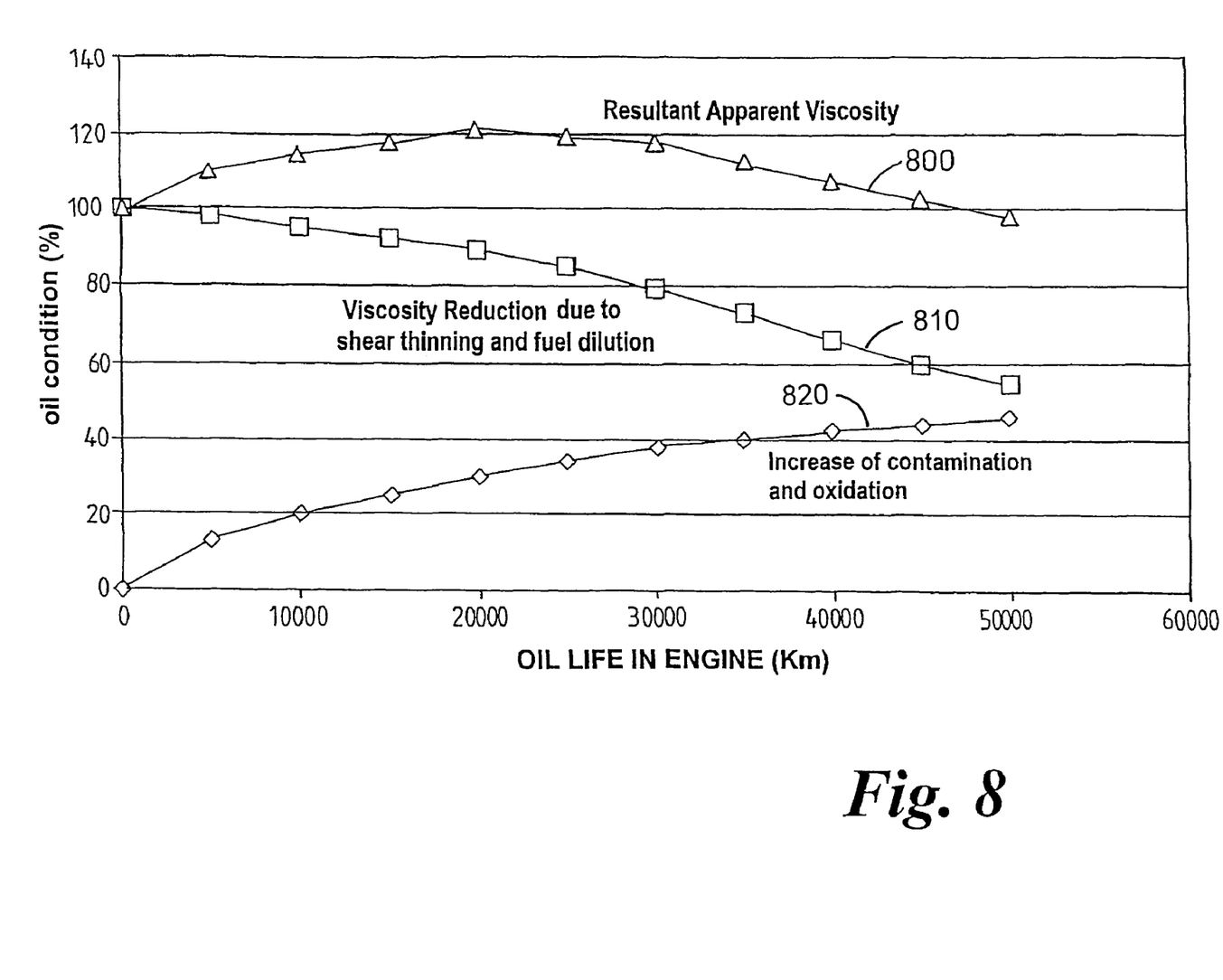
FIG. 8 is a graph showing how viscosity at a single temperature changes with increases in sooting and fuel dilution.

An example of the effects of ageing is illustrated in FIG. 8 of the accompanying drawings. Normal use of an oil in an engine may result in an increase in contamination due to sooting that has the effect of increasing the viscosity the viscosity may also be increased as a result of oxidation. At the same time any dilution of the oil will cause the viscosity to decrease as will shear thinning. The combined effect is shown by trace 800 in FIG. 8, showing an initial increase followed by a decrease of viscosity due to changes in shear thinning 810 and contamination 820.

Figure 9:
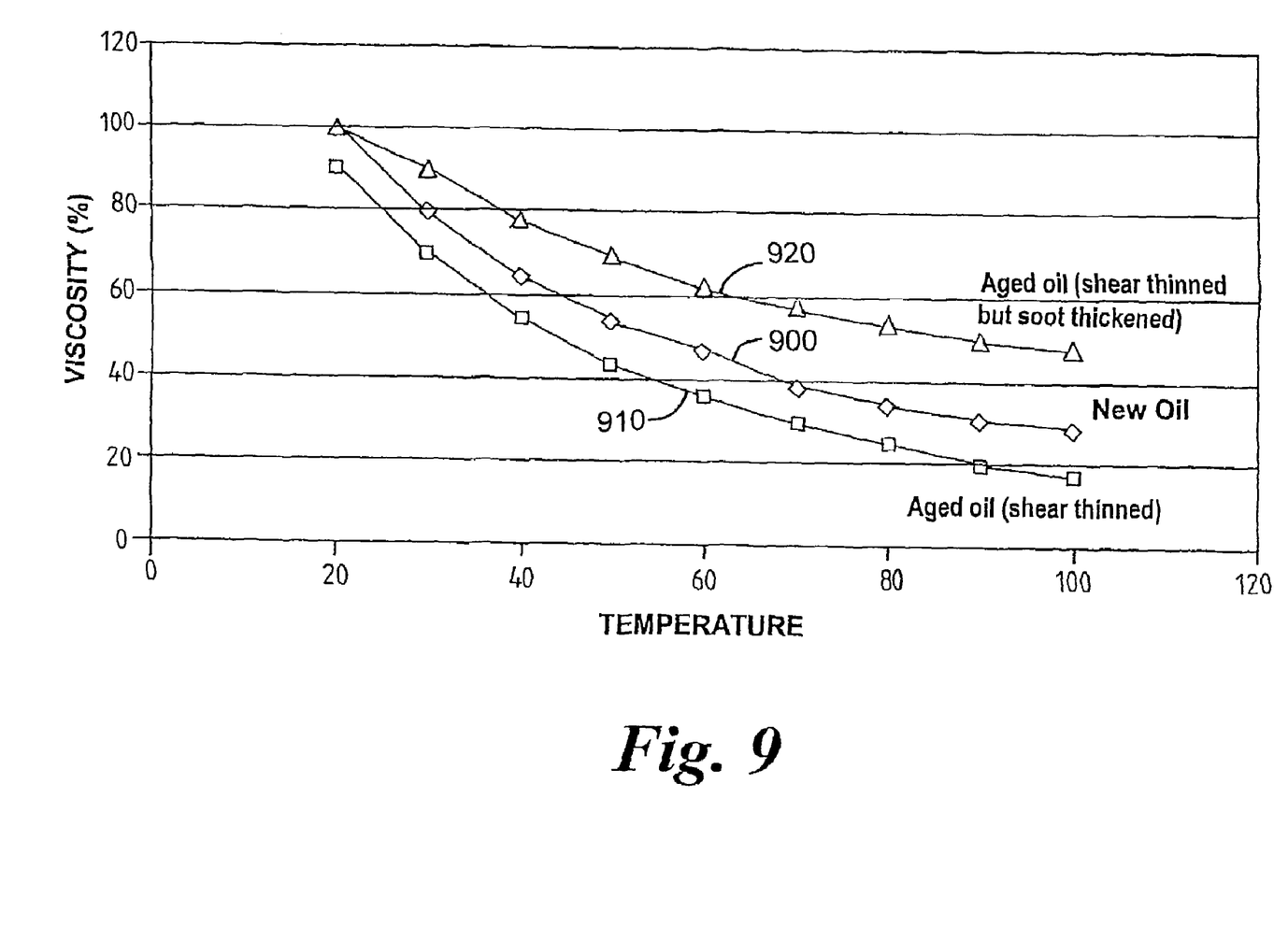
FIGS. 9 and 10 are plots of temperature versus viscosity taken at different periods of time to illustrate how different ageing effects change the shape of the temperature versus viscosity curves over time.
Figure 10:
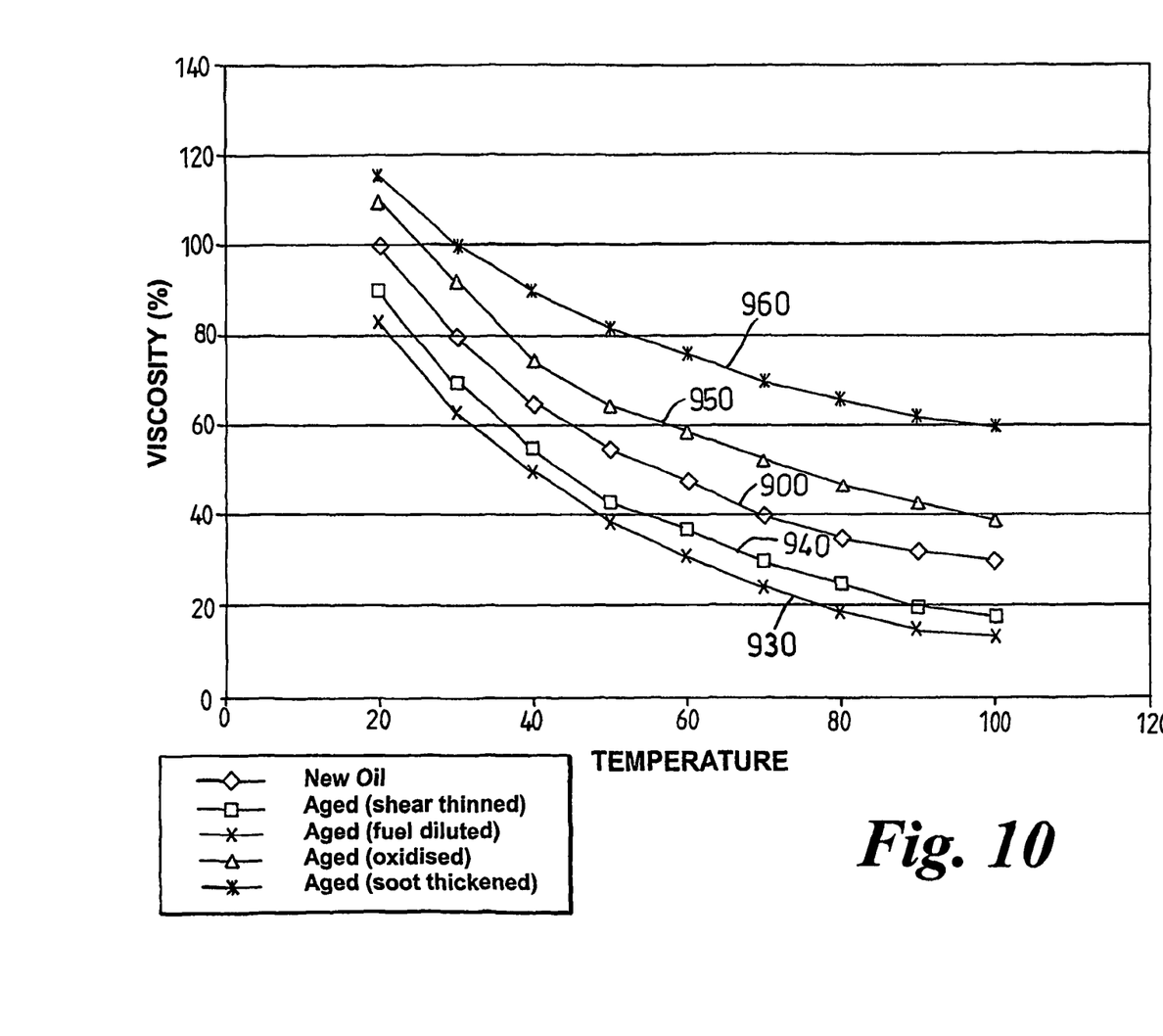

The simulated plots shown in FIGS. 9 and 10 show how the curves of temperature against viscosity vary from the first period (curve 900 ) to the second (curves 910 through 960) for different causes. The way in which each effect alters the shape of each curve is unique to that effect (or perhaps to a group of effects) allowing the effects to be identified.

In accordance with the provisions of the patent statutes, the principle and mode of operation of this invention have been explained and illustrated in its preferred embodiments. However, it must be understood that this invention may be practiced otherwise than as specifically explained and illustrated without departing from its spirit or scope.

What is claimed is:

1. An apparatus for measuring the viscosity and temperature of a fluid comprising:
   a transducer arranged to vibrate when provided with a drive signal of a given frequency to produce an ultrasonic shear wave;
   an impedance matching layer that is inserted into said fluid and which couples at least a first portion of said ultrasonic shear wave produced by said transducer into said fluid and from which at least a second portion of said ultrasonic shear wave is reflected back to said transducer;

a detector which is operative to detect a measurement signal produced by said transducer when said second reflected portion of wave is incident upon said transducer;

a control circuit which varies said frequency of said drive signal applied to said transducer and hence the frequency of said ultrasonic shear wave;

a processor which determines an optimum frequency of said drive signal at which said measurement signal produced by said transducer has its minimum amplitude; and a temperature determining means which estimates the temperature of said fluid as a function of said optimum frequency.

2. An apparatus according to claim 1 further including a look-up table in which an estimated temperature corresponding to a determined optimum frequency is stored.

3. An apparatus according to claim 2 further including a wave guide which has a first end and a second end, said wave guide being coupled to said transducer at said first end and to said impedance matching layer at said second end with said second end being inserted into said fluid to be measured and coupling said ultrasonic shear wave produced by said transducer into said fluid such that at least a portion of said wave is reflected back along said wave guide to said transducer.

4. An apparatus according to claim 3 wherein said wave guide includes a reflection interface located between said transducer and said matching layer from which a portion of said ultrasonic shear wave produced by said transducer is reflected back to said transducer to cause said transducer to produce a reference signal, said apparatus also including a detector to detect said reference signal and a reference signal monitoring circuit for measuring an amplitude of said reference signal.

5. An apparatus according to claim 4 further including a signal monitoring circuit for measuring an amplitude of said measurement signal and a comparator which compares amplitudes of said reference signal and its corresponding measurement signal to determine a viscosity of said fluid.

6. An apparatus according to claim 5 wherein the apparatus further includes a memory in which is stored a first set of measurements of viscosity of said fluid at a range of different temperatures obtained over a first period in time and a second set of measurements of viscosity of said fluid at a range of different temperatures obtained over a second, subsequent, period of time and further wherein said processor is operative to fit said first set of measurements to a first temperature/viscosity curve and said second set of measurements to a second temperature/viscosity curve and to then determine a cause of any viscosity changes with ageing of said fluid by comparing said second temperature/viscosity curve with said first temperature/viscosity curve.

7. An apparatus according to claim 5 wherein said wave guide includes a step decrease in cross section along its length.

8. An apparatus according to claim 7 wherein said wave guide comprises a cylindrical rod which has a step change in diameter along its length which defines a surface from which said reference signal is reflected.

* * * * *